United States Patent [19]
Gebe et al.

[11] Patent Number: 6,046,314
[45] Date of Patent: Apr. 4, 2000

[54] SPα: A NOVEL SCAVENGER RECEPTOR CYSTEINE-RICH DOMAIN-CONTAINING POLYPEPTIDE, AND MONOCLONAL ANTIBODIES THERETO

[75] Inventors: John A. Gebe, Kirkland; Anthony W. Siadak, Seattle, both of Wash.; Alejandro A. Aruffo, Belle Mead, N.J.

[73] Assignee: Bristol-Myers Squibb Co., Princeton, N.J.

[21] Appl. No.: 09/034,916

[22] Filed: Mar. 4, 1998

Related U.S. Application Data

[60] Provisional application No. 60/039,956, Mar. 6, 1997.
[51] Int. Cl.$^7$ .......................... C07H 21/04; C12N 15/12; C12N 15/63
[52] U.S. Cl. .................... 536/23.1; 435/69.1; 435/320.1; 435/325; 435/252.3; 435/172.3; 536/24.31
[58] Field of Search ................................ 435/69.1, 320.1, 435/325, 252.3, 172.3; 536/23.1, 24.31; 530/350

[56] References Cited

U.S. PATENT DOCUMENTS 5,508,164  4/1996  Kausch et al. ............................... 435/6

FOREIGN PATENT DOCUMENTS

WO 98/21328  5/1998  WIPO .

OTHER PUBLICATIONS

Aruffo et al., "The Lymphocyte Glycoprotein CD6 Contains a Repeated Domain Structure Characteristic of a New Family of Cell Surface And Secreted Proteins," *J. Exp. Med.* 174:949–952 (1991).

Bikah et al., "CD–5–Mediated Negative Regulation of Antigen Receptor–Induced Growth Signals in B–1 B Cells," *Science* 274: 1906–1909 (1996).

Freeman et al., "An Ancient, Highly Conserved Family of Cysteine–Rich Protein Domains Revealed by Cloning Type I and Type II Murine Macrophage Scavenger Receptors," *Proc. Natl. Acad. Sci. USA* 87:8810–8814 (1990).

Gangemi et al., "Anti–T12, An Anti–CD6 Monclonal Antibody, Can Activate Human T Lymphocytes," *J. Immunol.* 143:(8)2439–2447 (1989).

Jones et al., "Isolation of Complementary DNA Clones Encoding the Human Lymphocyte Glycoprotein T1/Leu–1," *Nature* 323:346–349 (1986).

Law et al., "A New Macrophage Differentiation Antigen Which is a Member of the Scavenger Receptor Superfamily," *Eur. J. Immunol.* 23:2320–2325 (1993).

Ledbetter et al., "Antibodies to Tp67 and Tp44 Augment and Sustain Proliferative Responses of Activated T Cells," *J. Immunol.* 135:(4)2331–2336 (1985).

Raab et al., "The T–Cell Antigen CD5 Acts as a Receptor and Substrate for the Protein–Tyrosine Kinase p56$^{lck}$," *Molecular and Cellular Biology* 14(5):2862–2870 (1994).

Resnick et al., "The SRCR Superfamily: A Family Reminiscent of the IG Superfamily," *Trends Biochem Sci.* 19:5–8 (1994).

Tarakhovsky et al., "Lymphocyte Populations and Immune Responses in CD5–Deficient Mice,"*Eur. J. Immunol.* 24:1678–1684 (1994).

Tarakhovsky et al., "A Role for CD5 in TCR–Mediated Signal Transduction and Thymocyte Selection," *Science* 269:535–537 (1995).

Whitney et al., "The Membrane–proximal Scavenger Receptor Cysteine–rich Domain of CD6 Contains the Activated Leukocyte Cell Adhesion Molecule Binding Site," *J. Of Biological Chemistry* 270(31):18187–18190(1995).

Wijngaard et al., "Molecular Characterization of the WC1 Antigen Expressed Specifically on Bovine CD4$^-$CD8$^-$γδ T Lymphocytes," *Journal of Immunology* 149(10):3273–3277 (1992).

Wijngaard et al., "Members of the Novel WC1 Gene Family are Differentially Expressed on Subsets of Bovine CD4$^-$CD8$^-$γδ T Lymphocytes," *J. Immunol.* 152:3476–3482 (1994).

Lin, C. C. et al., Differential Fluorescent Staining of Human Chromosomes with Daunomycin and Adriamycin—The D Bands, Science, vol. 190, pp. 61–63, 1975.

Gebe et al., "Molecular Cloning, Mapping to Human Chromosome 1 q21–q23, and Cell Binding Characteristics of SPα, a New Member of the Scavenger Receptor Cysteine–Rich (SRCR) Family of Proteins," *Journal of Biological Chemistry* 272(10):6151–6158 (1997).

Mayer et al., "A cDNA Clone from the Sea Lamprey Petromyzon Marinus Coding for a Scavenger Receptor Cys–Rich (SRCR) Protein," *Gene* 164:267–271 (1995).

Accession No. R99696, XP002072161 Hillier et al., "The WashU–Merk EST Project," (1995).

*Primary Examiner*—Elizabeth Kemmerer
*Assistant Examiner*—Nirmal S. Baji
*Attorney, Agent, or Firm*—Robins & Associates

[57] ABSTRACT

A new polypeptide from the scavenger receptor cysteine-rich family, termed Spα herein, as well as polynucleotides encoding Spα and methods of recombinantly producing the same, are disclosed. In addition, antibodies reactive with Spα are provided, as are methods of using antibodies that bind to Spα for modulating the interaction between Spα and its receptor. Immunoassay kits containing the anti-Spα antibodies are also provided.

5 Claims, 6 Drawing Sheets

FIG. 1A

```
                                            ┌─────────────  D3  ─────────────┐
                                            │                                │
 781  CCC TTT GAC TTG AGA CTA GTA GGA GGA GAC AAC CTC TGC TCT GGG CGA CTG GAG GTG CTG
 223  Pro Phe Asp Leu Arg Leu Val Gly Gly Asp Asn Leu Cys Ser Gly Arg Leu Glu Val Leu
 841  CAC AAG GGC GTA TGG GGC TCT GTC TGT GAT GAC AAC TGG GGA GAA AAG GAC CAG GTG
 243  His Lys Gly Val Trp Gly Ser Val Cys Asp Asp Asn Trp Gly Glu Lys Asp Gln Val
 901  GTA TGC AAG CAA CTG GGC TGT GGG AAG TCC CTC TCT AGA GAC TTC AGA GAC AAA TGC
 263  Val Cys Lys Gln Leu Gly Cys Gly Lys Ser Leu Ser Arg Asp Phe Arg Asp Lys Cys
 961  TAT GGC CCT GGG GTT GGC CGC ATC TGG CTG GAT AAT GTT CGT TGC TCA GGG GAG CAG
 283  Tyr Gly Pro Gly Val Gly Arg Ile Trp Leu Asp Asn Val Arg Cys Ser Gly Glu Gln
 1021 TCC CTG GAG CAG TGC CAG AGA CAC AGA TTT TGG GGG TTT CAC GAC TGC ACC CAC GAA GAT
 303  Ser Leu Glu Gln Cys Gln Arg His Arg Phe Trp Gly Phe His Asp Cys Thr His Glu Asp
 1081 GTG GCT GTC ATC TGC TCA GGA TAG CCT GGT GTT GCT TGA CCT GCT GCC CCT GGC CCC
 323  Val Ala Val Ile Cys Ser Gly
 1141 GCC TGC CCT CTG CTT GTT CTC CTG AGC CCT GAT TAT CCT CAT ACT CAT TCT GGG GCT CAG
 1201 GCT TGA GCC ACT ACT AGC CCC TCA CCT TGC CCT CAG TCC CTG GAA CAC TGG GCC TTA CTC
 1261 TCA GGG ACA AGC AGC CTT CCA CTT TGC ATC CTG TGC TAG ATG TCT GTT GCT GAG TTC GCT
 1321 GGG GAA GAT GAG CTT TTT CCA TTC CTT AAG CTG CCT GGA ATC CTC AAA CTG TGA CAC TGG
 1381 CCT TTC CTG TAA ATG TGC CAA CAT GGT TGA GAT CTG CTG TGT CAA ATC ACA ATG CTA ATC
 1441 GCA GAC CAT TAC AAA CAT TAT ATT GGT CTT CTG CTG TTG GTC TAG GTC TTA CTA ATC
 1501 TAT GTC TGC AAA ATT TCT CAA GCT AAT TCT TTC ATG TAA AGG AAT GAA ACA TTT GAA AGA AAA TGT GGG
 1561 TAG ACA ATT TCT CAA GCT AAT TCT ATG TAA AGG AAT CAC AGT TTA GAA ACA TTT TGA TTG GAC TAC TTT TTT
 1621 TTT TTT CCT CAA GGT GAC TCA GCT TGT CTT GAG GTT TGA GCT GTT TCT CTA TTC TGT TTC TTC CTA
 1681 GTG TAG GAC AAT TCT TTC AGG AGC GCG TCC TAT AAT CCT AGA CCT TTT CAT
 1741 GAC GTG TAA AAA ATG TTT CAT GGT GCC ATT CTG TGA GCC ACT TTT GTT GTC CAT
 1801 CCC TAT ACA ACC TGC CAA CAT GGT TGA CCA ATA AAA ATG AGA GGA ATG TCA AAA ATA CAT TTT
 1861 ACT TTA TTC AAA GAA ATA TTT GGT CTT GAA AAG GTC AAG AAA GAG GCA GAA AGA
 1921 GAT CAG GGG CTA AAG CTT TGT CTT ATG CCA AGT GGA AGT GGA AAA TAT CAC TTT TCA
 1981 CTT TAT CAA CTG AGA CTT CAA GGC TAA GCT TGA GGC AAG ACA ATA AGA GAA TCA
 2041 AGA CTT GAT TGT AAA AAT TGA CAA CTT TAG ATT CTG AGG CTA GGC TGA CTT ATT ATA
 2101 CGG CTA CAT TTA CAC ATT TAC ACT TAT CTA ATA AAT CAG ATT TCA CAA AAA AAA
 2161 AAA AAG AAA AAA AAA AAA AAA
```

SPα: A NOVEL SCAVENGER RECEPTOR CYSTEINE-RICH DOMAIN-CONTAINING POLYPEPTIDE, AND MONOCLONAL ANTIBODIES THERETO

CROSS-RELATED TO RELATED APPLICATION

This application is related to provisional patent application Ser. No. 60/039,956, filed Mar. 6, 1997, from which priority is claimed under 35 USC §119(e)(1) and which is incorporated herein by reference in its entirety.

TECHNICAL FIELD

The invention relates generally to immunoregulatory polypeptides. More particularly, the invention relates to a novel scavenger receptor cysteine-rich domain-containing polypeptide, designated Spα, and to oligonucleotides encoding the Spα polypeptide. In addition, the invention relates to antibodies reactive with Spα, and methods of using such antibodies to modulate the interaction between Spα and its receptor and to identify other molecules that modulate this interaction.

BACKGROUND OF THE INVENTION

A discrete number of cell surface antigens and secreted antigens are known to regulate leukocyte function. In particular, these antigens govern leukocyte activation, proliferation, survival, cell adhesion and migration, effector function, and the like. Among those antigens that have been shown to regulate leukocyte function are members of the scavenger receptor cysteine-rich ("SRCR") domain-containing protein family. Members of this protein family have conserved sequence motifs that are characterized by short, disulfide-stabilized domains.

The SRCR domain was initially recognized during the analysis of the structure of the type I macrophage scavenger receptor in which a motif of approximately 101 amino acid residues was identified. The SRCR domain defines an ancient, highly conserved family of cysteine-rich proteins and is present in CD5 and CD6 molecules (Freeman et al. (1990), *Proc. Natl. Acad. Sci USA* 87:8810).

The SRCR family of proteins can be divided into two groups, designated group A and group B. The groups may be distinguished primarily by the presence of 6 (group A) or 8 (group B) positionally conserved cysteine residues within each SRCR domain, however, proteins having 6 such residues within each SRCR domains have also been characterized as group B proteins at least in part by the presence of cysteine residues at the $C^1$ and $C^4$ positions (Resnick et al. (1994) *Trends Biochem. Sci.* 19:5–8). Independent SRCR consensus sequences for groups A and B, as well as a combined consensus sequence, have been identified (see, Resnick et al. (1994), supra). Group B includes the cell surface proteins CD5 (Jones et al. (1986) *Nature* 323:346–349) and CD6 (Aruffo et al. (1991) *J. Exp. Med.* 174:949–952), which are predominantly expressed by thymocytes, mature T cells and a subset of B cells, WC1 (Wijngaard et al. (1992) *J. Immunol.* 149:3273–3277; Wijngaard et al. (1994) *J. Immunol.* 152:3476–3482), which is expressed by γδ T cells in cattle, and M130 (Law et al. (1993) *Eur. J. Immunol.* 23:2320–2325), which is expressed by activated monocytes.

Monoclonal antibody (mAb) crosslinking studies suggest that both CD5 and CD6 can function as accessory molecules capable of modulating T cell activation (Gangemi et al. (1989) *J. Immunol.* 143:2439–2447; Ledbetter et al. (1985) *J. Immunol.* 135:2331–2336). This role of CD5 and CD6 in the regulation of T cell function is supported by the finding that, following T cell activation, tyrosine residues in the cytoplasmic domain of these two proteins are transiently phosphorylated. This would provide a molecular mechanism by which the cytoplasmic domains of both CD5 and CD6 can interact with intracellular SH2 containing proteins involved in signal transduction (Raab et al. (1994) *Mol. Cell. Biol.* 14:2862–2870). Furthermore, phenotypic analysis of a CD5-deficient murine strain showed that its T cells are hyper-responsive to stimulation (Tarakhovsky et al. (1994) *Eur. J. Immunol.* 24:1678–1684; Tarakhovsky et al. (1995) *Science* 269:535–537), suggesting that CD5 expression is required for the normal regulation of T cell receptor-mediated T cell activation. In addition, comparison of anti-immunoglobulin M-induced growth responses in B-1 and B-2 cells from wild-type or CD5-deficient mice indicated that CD5 acts as a negative regulator of membrane immunoglobulin M-mediated signaling in B-1a cells.

Bikah et al. (1996) *Science* 274:1906–1909. These authors suggested that certain autoimmune states may be due to defects in CD5-mediated negative regulation of membrane IgM signaling.

CD5 and CD6 are structurally the most closely related members of the group B SRCR family of proteins (Resnick et al., supra). They are both type I membrane proteins whose extracellular region is composed of three SRCR-like domains each containing 8 cysteine residues which are thought to form intrachain disulfide bonds. The extracellular domains of CD5 and CD6 are anchored to the cell membrane via a hydrophobic transmembrane domain and a long cytoplasmic domain. It has been reported that CD5 binds to the B cell antigen CD72 and to CDSL, an antigen which is transiently expressed by activated B cells which has yet to be fully characterized. CD6 has been shown to bind to the leukocyte activation antigen, activated leukocyte cell adhesion molecule ("ALCAM"). Unlike CD5 and CD6, which are closely related, CD72 and ALCAM are not homologous. CD72 is a type II membrane protein which is homologous to the C-type lectins, however, a lectin activity for CD72 has not been reported. ALCAM is a type I membrane protein whose extracellular region is composed of five Ig-like domains (Bowen et al. (1995) *J. Exp. Med.* 181:2213–2220). The regions of CD5 and CD72 involved in their interaction have not been identified. Studies with truncated forms of both CD6 and ALCAM have shown that the interaction between these two proteins is primarily mediated by the membrane proximal SRCR domain of CD6 and the amino terminal Ig-like domain of ALCAM (Whitney et al. (1995) *J. Biol. Chem.* 270:18187–18190; Bowen et al. (1996) *J. Biol. Chem.* 271:17390–17396).

The identification of a novel molecule involved in leukocyte function provides a new target for monitoring immunoregulatory function and for therapeutic intervention therewith.

SUMMARY OF THE INVENTION

The inventors herein have identified and cloned a new SRCR domain-containing polypeptide, designated "Spα." Spα is a secreted protein and is homologous to CD5 and CD6. Spα has the same domain organization as the extracellular region of CD5 and CD6 and is composed of three SRCR domains. As shown herein, RNA transcripts encoding Spα were found in human bone marrow, spleen, lymph node, thymus and fetal liver but not in non-lymphoid tissues. Binding studies with an Spα-immunoglobulin (Ig) fusion protein showed that Spα was capable of binding to cells of the monocytic lineage including freshly elutriated monocytes, the premonocytic cell line K-562, and the myeloid cell line THP-1. Spα also bound to the B cell line Raji and the T cell line Hut78. Spα appears to be involved in the regulation of monocyte activation, function and/or survival, and is therefore an important component in the immunoregulatory system.

Accordingly, in one embodiment, the invention is directed to a polynucleotide that encodes an Spα polypeptide.

In another embodiment, the invention is directed to a recombinant vector comprising such a polynucleotide molecule.

In still other embodiments, the invention is directed to recombinant host cells transformed with vectors comprising the DNA and methods of producing recombinant polypeptides using the transformed cells.

In another embodiment, the invention is directed to an isolated Spα polypeptide.

In yet another embodiment of the invention, antibodies to the Spα polypeptide are provided.

In yet a further embodiment, the invention is directed to a method of modulating the interaction between the Spα polypeptide and the Spα polypeptide receptor.

These and other embodiments of the present invention will readily occur to those of ordinary skill in the art in view of the disclosure herein.

BRIEF DESCRIPTION OF THE FIGURES

FIGS. 1A–1B depict the DNA sequence encoding Spα (SEQ ID NO: 1) and the corresponding deduced amino acid sequence (SEQ ID NO: 2). Underlined amino acid sequences denote SRCR domains. Conserved cysteine residues are shown in bold italics. Polyadenylation sites are double underlined and adenylate/uridylate-rich elements ("AREs") are shaded.

FIG. 2 depicts a comparison of the amino acid sequences of SRCR domains of Spα, M130 and CD6 (SEQ ID NOS: 3–17). The individual domains are indicated as D1, D2, etc. Gaps were introduced to maximize homology, and are represented by dots. Amino acids are represented by their single letter code. Conserved cysteine residues are enclosed in boxes. Gray highlighted areas are regions in which 11 out of 15 amino acids are homologous.

DETAILED DESCRIPTION

Figure 3:
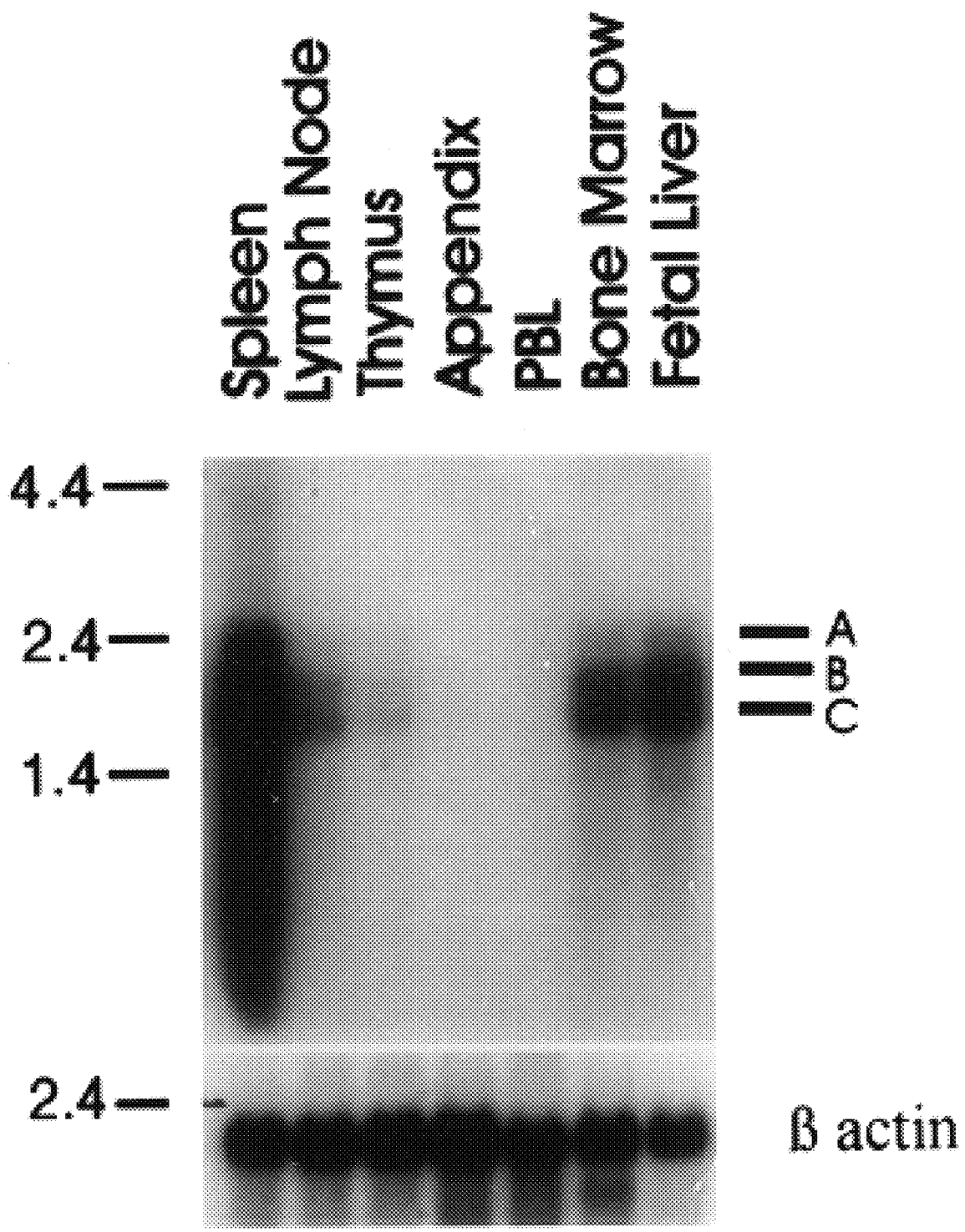
FIG. 3 depicts the results of a tissue Northern blot showing the RNA messages hybridizing to Spα. Markings of A, B, and C indicate the three bands which hybridize to Spα.

The practice of the present invention will employ, unless otherwise indicated, conventional techniques of protein chemistry and biochemistry, molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

Figure 1A:
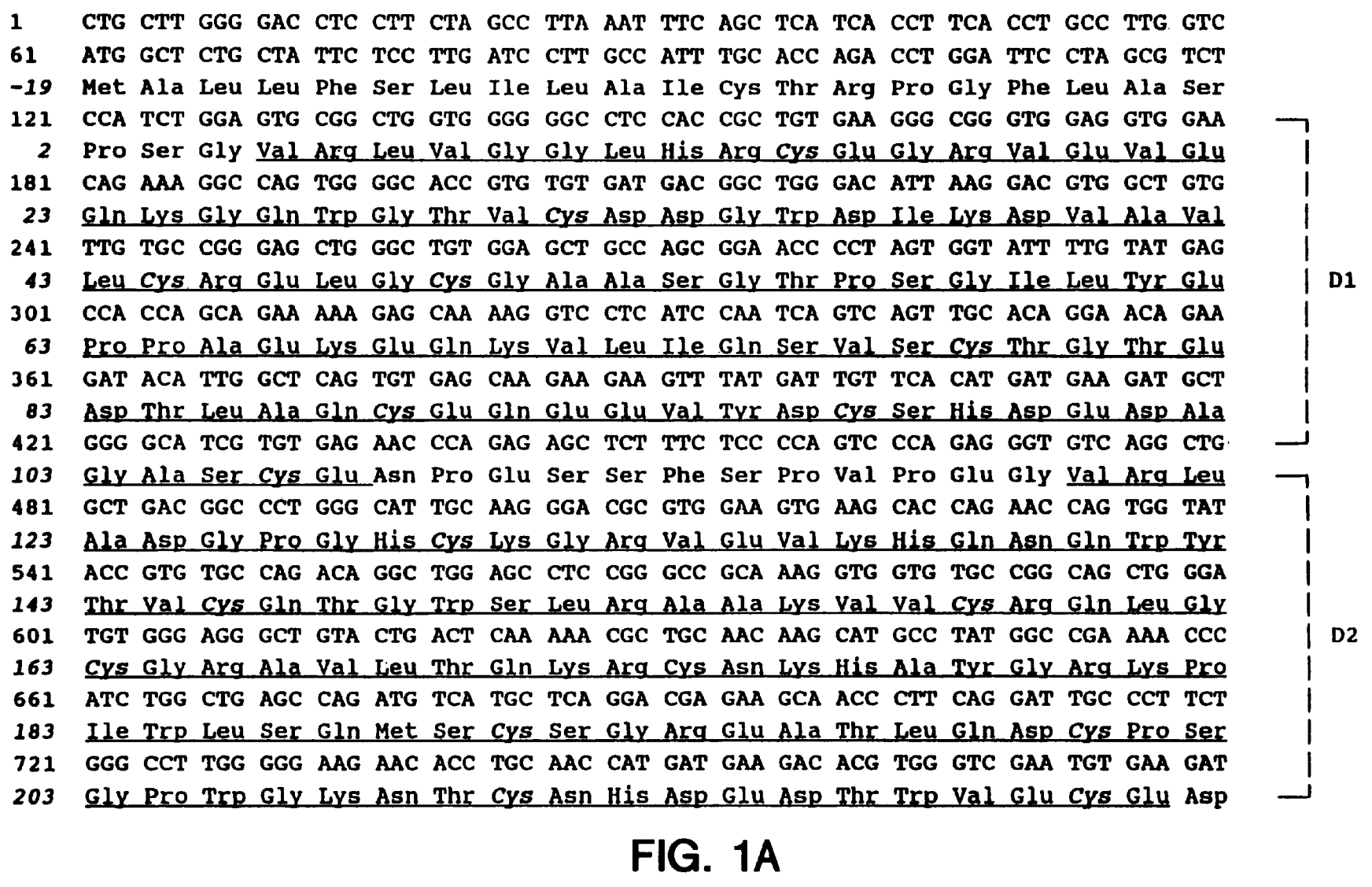

The terms "polypeptide", "peptide" and "protein" are used interchangeably and refer to any polymer of amino acids (dipeptide or greater) linked through peptide bonds. Thus, the terms "polypeptide", "peptide" and "protein" include oligopeptides, protein fragments, analogs, muteins, fusion proteins and the like. Thus, by "Spα polypeptide" is meant a polypeptide, whether isolated, recombinant or synthetic, comprising an amino acid sequence identical to that depicted in FIG. 1, and fragments thereof that include only so much of the molecule as necessary for the polypeptide to retain biological activity, e.g., catalytic and/or immunological activity, as well as analogs that are substantially homologous thereto, mutated or variant proteins, and the like, thereof that retain such activity.

Two polynucleotide or polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified polypeptide sequence. Nucleic acid sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra. Such sequences can also be confirmed and further characterized by direct sequencing of PCR products. Other techniques for determining nucleic acid and amino acid sequence identity are well known in the art and include determining the nucleotide sequence of the mRNA for the gene of interest (usually via a cDNA intermediate) and determining the amino acid sequence encoded thereby, and comparing this to a second amino acid sequence. Programs for calculating both the identity between two polynucleotides and the identity and similarity between two polypeptide sequences are available in the Wisconsin Sequence Analysis Package, Version 8 (available from Genetics Computer Group, Madison, Wis.) for example, the GAP program. Other programs for calculating identity or similarity between sequences are known in the art.

By the term "degenerate variant" is meant a polynucleotide containing changes in the nucleic acid sequence thereof, such as insertions, deletions or substitutions, that encodes a polypeptide having the same amino acid sequence as the reference polypeptide from which the degenerate variant is derived.

By the phrase "antibody reactive with an Spα polypeptide" is meant an antibody, either polyclonal or monoclonal, specific for an Spα polypeptide, or specific for a protein homologous thereto. Such reactivity can be determined by immunoprecipitation and Western blot analysis, using methods well known in the art. Such an antibody denotes not only the intact molecule, but also active fragments thereof, retaining specificity for the Spα polypeptide. (See, e.g., Baldwin, R. W. et al. in *Monoclonal Antibodies for Cancer Detection and Therapy* (Academic Press 1985) for a description of the production of antibody fragments.) The phrase also contemplates chimeric antibodies that retain specificity for the Spα protein in question. In particular, the antibody can include the variable regions or fragments of the variable regions which retain specificity for the Spα molecule. The remainder of the antibody can be derived from the species in which the antibody will be used. Thus, if the antibody is to be used in a human, the antibody can be "humanized" in order to reduce immunogenicity yet retain activity. For a description of chimeric antibodies, see, e.g., Winter, G. and Milstein, C. (1991) *Nature* 349:293–299; Jones et al. (1986) *Nature* 321:522–525; Riechmann et al. (1988) 332:323–327; and Carter et al. (1992) *Proc. Natl. Acad. Sci. USA* 89:4285–4289. The phrase also includes other recombinant antigen-binding molecules that bind to Spα including single-chain antibodies, bispecific antigen-binding molecules in which at least one variable region binds to Spα, and the like.

"Recombinant" as used herein to describe a polynucleotide means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A "vector" is a replicon, i.e., a genetic element that behaves as an autonomous unit of polynucleotide replication within a cell, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA sequences, genomic DNA sequences, and even synthetic DNA sequences. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "heterologous" region of a DNA construct is an identifiable segment of DNA within or attached to another DNA molecule that is not found in association with the other molecule in nature. Thus, when the heterologous region encodes a human gene, the gene will usually be flanked by DNA that does not flank the human gene in the human genome. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The following single-letter amino acid abbreviations are used throughout the text:

| Alanine | A | Arginine | R |
|---|---|---|---|
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

B. General Methods

Central to the present invention is the discovery of a polynucleotide that encodes an Spα polypeptide. The secreted polypeptide has been characterized as containing three SRCR domains. Spα is capable of binding to myeloid cell lines and cells of monocytic origin. RNA blot analysis indicates that transcripts encoding Spα are exclusively expressed in lymphoid tissues and that Spα is involved in processes responsible for both the development and maintenance of the lymphoid compartment.

The observation that Spα binds to peripheral monocytes, and the recognition that other secreted polypeptides, such as cytokines, have immunoregulatory function, clearly implicates a similar function for Spα.

In addition, Spα, or modulation of interactions involving Spα, may be used in regulating the inflammatory response. Spα is capable of upregulating the Spα polypeptide receptor on monocyte-like THP1 cells and of differentiating THP1 cells from a nonadherent state to an adherent state. Vascular endothelium plays an active role in inflammatory leukocyte recruitment via expression of adhesion molecules and chemoattractant cytokines. These inducible effectors appear to be important determinants of characteristics of acute and chronic inflammatory reactions. Accordingly, preventing the interaction of Spα with its ligand, e.g., with an appropriately targeted antibody or other molecule, should prevent upregulation of adhesion molecules on the cell surface. Such inhibition of upregulation of cell-surface adhesion molecules would prevent movement of these cells from the peripheral into surrounding tissue, and therefore provide a means to regulate such events as monocyte/macrophage-related wound healing and inflammatory responses.

The Spα polypeptide of the present invention may be synthesized by conventional techniques known in the art, for example, by chemical synthesis such as solid phase peptide synthesis. In general, these methods employ either solid or solution phase synthesis methods. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis*, Biology, supra, Vol. 1, for classical solution synthesis. Polypeptides containing either L- or D-amino acids may be synthesized in this manner. Polypeptide composition is confirmed by quantitative amino acid analysis and the specific sequence of each peptide may be determined by sequence analysis.

Alternatively, the Spα polypeptide can be produced by recombinant techniques by providing DNA encoding the Spa polypeptide, along with an ATG initiation codon. Based on knowledge of the amino acid sequence, DNA encoding Spα can be derived from genomic or cDNA, prepared by synthesis, or by a combination of techniques. The DNA can then be used to express Spα or as a template for the preparation of RNA using methods well known in the art (see, Sambrook et al., supra).

More specifically, DNA encoding Spα may be obtained from an appropriate DNA library or a cDNA library prepared from an mRNA isolated from an appropriate source, e.g., a human spleen mRNA. DNA libraries may be screened using the procedure described by Grunstein et al. (1975) *Proc. Natl. Acad. Sci. USA* 73:3961. Synthetic oligonucleotides may be prepared using an automated oligonucleotide synthesizer such as that described by Warner (1984) *DNA* 3:401.

Once coding sequences for the Spα polypeptide have been synthesized or isolated, they can be cloned into any suitable vector for expression. Numerous cloning vectors are known to those of skill in the art, and the selection of an appropriate cloning vector is a matter of choice. Examples of recombinant DNA vectors for cloning and host cells which they can transform include, but are not limited to, bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra. Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence which cause the secretion of the expressed polypeptide from the host organism. Leader sequences can be removed by the host in post-translational processing. See, e.g., U.S. Pat. Nos. 4,431, 739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the polypeptide of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. The proteins may also be expressed in Trypanosomes.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by high performance liquid chromatography ("HPLC"). Other methods of amino acid sequencing are also known in the art.

In addition, the sequences disclosed herein can also be used to design oligonucleotide probes to detect the presence of Spα or similar genes in other species, tissues and cell types, e.g., for cloning or diagnostic purposes. In particular, genomic and cDNA libraries, derived from the desired tissue, can be prepared using techniques well known in the art. Oligonucleotide probes which contain the codons for a portion of the determined sequence can be prepared and used to screen the libraries for these and homologous Spα genes. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert indeed contains an SPα gene and the gene can be isolated. See, e.g., Sambrook et al., supra. Isolated genes encoding an Spα polypeptide can be cloned into any suitable vector for expression as described above.

Spα polypeptides can be used in pharmaceutical compositions for modulating the immune response in, for example, autoimmune diseases, viral infections, transplant rejection suppression, tumor cell proliferation suppression, combined variable immunodeficiency, and the like. The Spα polypeptide of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tumor in question, or to a site of inflammation, e.g., direct injection into an arthritic joint, will also find use with the present invention.

Therapeutically effective doses will be easily determined by one of skill in the art and will depend on the severity and course of the disease, the patient's health and response to treatment, and the judgment of the treating physician.

The Spα polypeptide of the present invention, or fragments thereof, can also be used to produce antibodies, both polyclonal and monoclonal. If polyclonal antibodies are desired, a selected mammal, (e.g., mouse, rabbit, goat, horse, pig etc.) is immunized with an antigen of the present invention, or its fragment, or a mutated antigen. Serum from the immunized animal is collected and treated according to known procedures. If serum containing polyclonal antibodies is used, the polyclonal antibodies can be purified by a variety of methods, such as by immunoaffinity chromatography, using known procedures.

Monoclonal antibodies to the Spα proteins, and to the fragments thereof, can also be readily produced by one skilled in the art using, e.g., hybridoma technology. The general methodology for making monoclonal antibodies by using hybridoma technology is well known. For example, immortal antibody-producing cell lines can be created by cell fusion, as well as by other techniques such as direct transformation of B lymphocytes with oncogenic DNA, or transfection with Epstein-Barr virus. See, e.g., M. Schreier et al. *Hybridoma Techniques* (1980); Hammerling et al. *Monoclonal Antibodies and T-cell Hybridomas* (1981); Kennett et al. *Monoclonal Antibodies* (1980); U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the Spα proteins can be screened for various properties; i.e., for isotype, epitope, affinity, etc.

The antibodies generated against the Spα proteins can be used in standard immunoassays, as diagnostic reagents, to screen tissues and/or tumors for the presence or absence of the proteins, or for the presence or absence of aberrant Spα proteins, to screen for molecules that modulate the interaction between Spα and its ligand, or the like. In addition, antibodies that bind to an Spα can themselves be used to modulate the interaction between Spα and its ligand, thereby modulating the immunoregulatory effect of Spα.

For example, the presence of Spα proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as enzyme-linked immunosorbent assays ("ELISAs"); biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the Spα proteins and the antibodies described above.

Assays can also be conducted in solution, such that the Spα proteins and antibodies thereto form complexes under precipitating conditions. The precipitated complexes can then be separated from the test sample, for example, by centrifugation. The reaction mixture can be analyzed to determine the presence or absence of antibody-Spα complexes using any of a number of standard methods, such as those immunodiagnostic methods described above.

The Spα proteins and antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Cloning of Spα: Full-length cDNAs were cloned from a human spleen library (Clontech HL5011a) by plaque hybridization. Approximately $1 \times 10^6$ clones were plated onto 20 plates and transferred to Hybond N+ nylon membranes (Amersham rpnl32b) according to the manufacturer's instructions. Membranes were crosslinked by exposure to ultraviolet radiation and then hybridized by the method of Church et al. (1984) Proc. Natl. Acad. Sci. USA 81:1991–1995. All hybridizations were done with a radio-labeled EcoR1 fragment digested from the partial Spα cDNA obtained from the expressed sequence tag ("EST") clone number 201340 (Research Genetics). The EcoRI fragment contained base pairs 1–1594 and was radiolabeled with $\gamma$-[$^{32}$P]-dCTP (Amersham) using a random labeling kit (Boehringer Mannheim). Membranes were washed at 60° C. using high stringency wash buffer and exposed to Kodak X-ray film (X-OMAT AR). A subset of positive plaques were then replated and rescreened. After three rounds of screening ten individual clones were obtained, two of which were full-length. Both of these full-length clones were sequenced in both directions using the dideoxy method (Sanger et al. (1977) Proc. Natl. Acad. Sci. USA 74:5463).

Northern Blot: Two tissue and one cell line Northern blots were purchased from Clontech (catalog nos. 7766-1, 7754-1 and 7757-1, respectively) and hybridized in 50% formamide at 42° C. according to the manufacture's instructions. Radiolabeled Northern blot probes were prepared as outlined above. mRNA normalization probes were either GAPDH or β-actin. Positive blots were washed under high stringency conditions. Blots were exposed to Kodak X-ray film (X-OMAT AR).

Fusion Protein Constructs: DNA corresponding to the translated region of Spα was obtained by polymerase chain reaction ("PCR") using full-length Spα cDNA as template. Primers were designed with restriction sites enabling Spα C-terminal ligation to the hinge, CH2, and CH3 domains of murine IgG2a (mIg). All constructs were sequenced to verify the correctness of the sequence and the reading frames. Spα-mIg (in the CDM8 expression vector) was transiently expressed in COS cells (Aruffo et al. (1990) Cell 61:1303–1313). The soluble Spα-mIg was purified from the COS cell supernatant by Protein-A column chromatography. Following Protein-A binding, the column was washed extensively with phosphate buffered saline ("PBS"), pH 7.0, and eluted with 4.0 M imidazole, pH 8.0, containing 1 mM each of $MgCl_2$ and $CaCl_2$. Eluted proteins were dialyzed extensively with PBS.

Cell Culture: Human cell lines were grown to 0.5–0.9× $10^6$ cells/ml in Iscove's Modified Dulbecco's Medium ("IMDM") containing 10% fetal bovine serum. Human peripheral blood T, B and monocytes cells were separated by counterflow centrifugal elutriation.

Flow Cytometry: Approximately $5 \times 10^5$ cells were incubated on ice for one hour in 100 µl stain buffer (PBS containing 2% bovine serum albumin, fraction V, 0.05% sodium azide, 1 mM each $MgCl_2$ and $CaCl_2$) containing 20 µg/ml Spα-mIg fusion protein and 200 Ig/ml human IgG (Sigma catalog no. I-8640). Cells were then washed with stain buffer, centrifuged and aspirated. Following a second wash, cells were incubated on ice for one hour in 100 µl stain buffer containing 1:100 diluted fluorescein isothiocyanate ("FITC")-labeled rabbit anti-mouse IgG2a antibody (Zymed catalog no. 61-0212). Cells were than washed twice and resuspended in 0.5 ml stain buffer. Samples were run on a Beckton-Dickinson Facscan. Prior to running samples, propidium iodide ("PI") was added to 1 µg/ml. Dead cells were identified as PI positive and were gated out and not used in the analysis. Mouse antibodies specific for CD3 (64.1 generously donated by Jeff Ledbetter, Ph.D., Bristol-Myers Squibb, T cell), CD19 (IOB4a Amak 1313, B cell), and CD14 (MY4 Coulter 6602622, monocytes) were used to verify elutriated cells. Second step staining for these antibodies was a FITC-labeled goat anti-mouse IgG (Bioscience 4408).

EXAMPLE 1

Cloning of Spα

New members of the SRCR family of proteins were isolated as follows. Screening of DNA data bases identified a cDNA fragment from the human EST data base that exhibited extensive sequence homology with members of the SRCR group B proteins including CD5, CD6, M130 and WC1. The EST sequence (from fetal liver-spleen) was used as a probe to screen a cDNA library prepared from mRNA isolated from a human spleen. This resulted in the isolation of ten cDNA clones. The two longest clones, 1804 bp and 2152 bp respectively, were sequenced in both orientations and found to contain a long open reading frame that encoded a 347 amino acid polypeptide, named Spα, which has features of a secreted protein. The cDNA sequence encoding Spα, and the deduced amino acid sequence thereof are shown in FIGS. 1A–1B (SEQ ID NOS: 1–2)

Figure 2:
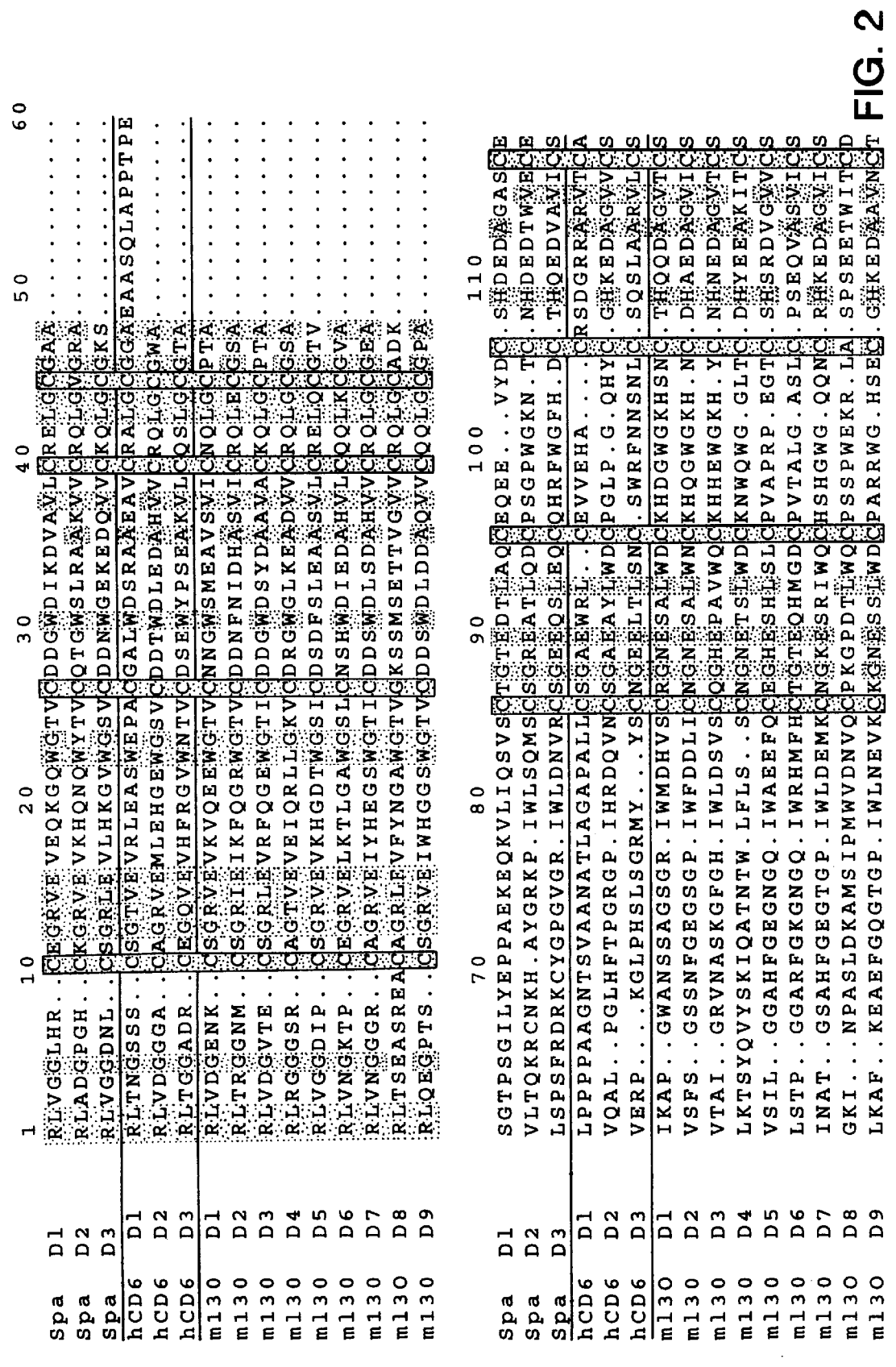

Spα contains an amino-terminal sequence of 19 hydrophobic amino acids which acts as a secretory signal sequence and are removed from the mature protein, as indicated by the N-terminal sequence of the Spα immunoglobulin fusion protein produced by COS cells. This putative secretory signal sequence is followed by three cysteine-rich domains, each of approximately 100 amino acids. As shown in FIG. 2, the cysteine-rich domains are significantly homologous to the cysteine-rich domains found in the SRCR group B family of proteins (Resnick et al. (1994) Trends Biochem. Sci. 19:5–8). The third SRCR domain of Spα is followed by an in-frame stop codon.

The SRCR domains of Spα exhibit approximately 40% to 48% identity, i.e., same amino acid-same position identity, with the corresponding domains of CD5, CD6, WC1 and M130. In addition, Spα contains the eight conserved cysteine resides that identify it as a member of the group B family. However, unlike other members of the group B family, Spα does not contain a transmembrane domain. Furthermore, the predicted amino acid sequence of Spα contained no putative N-linked glycosylation sites.

The two Spα clones differed from one another in two respects. First, there is a single base pair difference between the two clones at position 968. The change of a T to a C is located within the coding sequence but does not result in a change in the predicted amino acid sequence of Spα. Second, the two clones differ in the length of their 3' untranslated regions, one clone having a 3'UTR that is 348 bp longer than the other. The shorter clone has a poly-A sequence starting 18 bases downstream from a consensus polyadenylation sequence. The longer clone has two polyadenylation consensus sequences: the first sequence is identical to the polyadenylation consensus sequence found in the shorter clone; and the second sequence is located 351 bp downstream from the first poly-adenylation site. The longer clone also contains three adenylate/uridylate-rich elements (AREs; AUUUA) in the 3' untranslated sequence. The three AREs are located between the two poly-adenylation sites. ARE elements are located within the 3' untranslated region of mRNAs and have been found to be the most common determinant of RNA stability (Shaw et al. (1986) *Cell* 46:659–667; Chen et al. (1995) *Trends Biochem. Sci.* 20:465–470). Messenger RNAs encoding cytokines and transcription factors, among others, contain these elements which provide an additional mechanism for the regulation of protein expression by directing the stability and therefore half-life of the mRNA encoding the protein. The finding that at least one of the mRNAs encoding Spα contains ARE motifs suggests that the expression of this protein might be tightly regulated.

Comparison of Spα with other members of the SRCR group B family showed that its SRCR domains are most closely related to those found in M130 (FIG. 2). However, Spα most closely resembles CD5 and CD6 in its domain organization. Both CD5 and CD6 are cell surface proteins whose extracellular domains are composed of three SRCR domains.

EXAMPLE 2

Identification of Tissues Expressing mRNA Transcripts Encoding Spα

RNA blot analysis using a Spα cDNA fragment as a probe indicated that mRNA encoding Spα is expressed in the spleen, lymph nodes, thymus, bone marrow, and fetal liver but not in prostate, testis, uterus, small intestine, colon, peripheral blood leukocytes and appendix (FIG. 3). In all cases, tissues expressing mRNA transcripts encoding Spα expressed three hybridizing transcripts. These transcripts are approximately 2.4, 2.1, and 1.8 kbp in length. The 1.8 kbp and 2.1 kbp transcripts correspond in length to the two longest cDNAs isolated from the spleen cDNA library. The finding that two of the isolated cDNAs have sizes consistent with those seen in the RNA blot suggest that they may all encode Spα, but differ from one another in the length of their untranslated regions. It should be noted that the possibility that one or more of these transcripts may encode closely related proteins cannot be excluded by these data. To determine which cells produce Spα, several cell lines were analyzed by Northern blot. The RNA message for Spα was not detected in the following cell lines: HL60, K562, Raji, Molt4, A549, SW480, GA36 1, HeLa S3, and peripheral blood leukocytes.

The RNA blot analysis indicates that transcripts encoding Spα are exclusively expressed in lymphoid tissues. By contrast, leukocytes do not appear to express this protein. These findings suggest that Spα may be produced by specialized epithelial and or endothelial cells in lymphoid tissues. The observation that Spα is expressed in bone marrow, thymus and fetal liver as well as in the spleen and lymph nodes implicates this protein in processes responsible for both the development and maintenance of the lymphoid compartment.

EXAMPLE 3

Binding of Spα-mIg to Myeloid Cell lines and Monocytes

Previously, an immunoglobulin (Ig) fusion approach had been used to identify cells expressing a CD6 ligand (Wee et al. (1994) *Cell. Immunol.* 158:353–364). These studies led to the isolation of a cDNA encoding a CD6 ligand referred to as ALCAM (Bowen et al. (1995) *J. Exp. Med.* 181:2213–2220). Using this same approach, an Ig fusion protein containing only the membrane proximal SRCR domain of CD6, CD6D3-Ig, was shown to be capable of binding to ALCAM (Whitney et al. (1995) *J. Biol. Chem.* 270:18187–18190). This same approach was used herein to identify cells which express an Spα receptor(s).

Figure 4A:
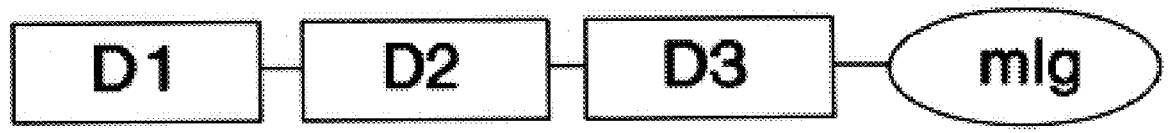
FIG. 4A depicts an Spα fusion immunoglobulin construct as described in Example 4. D1, D2, and D3 are the SRCR domains, and mIg is the mouse immunoglobulin portion containing the hinge, CH2 and CH3 domains.
Figure 4B:
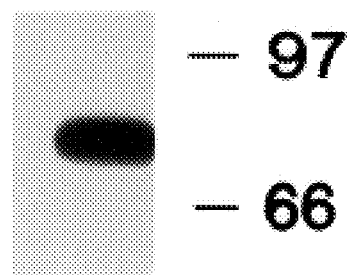
FIG. 4B is a photograph of 12% SDS page gel electrophoresis of the fusion polypeptide.

A full-length Spα-mIg fusion protein (FIG. 4A) was produced by transient expression in COS cells and expressed as covalent homodimer (FIG. 4B).

Figure 5:
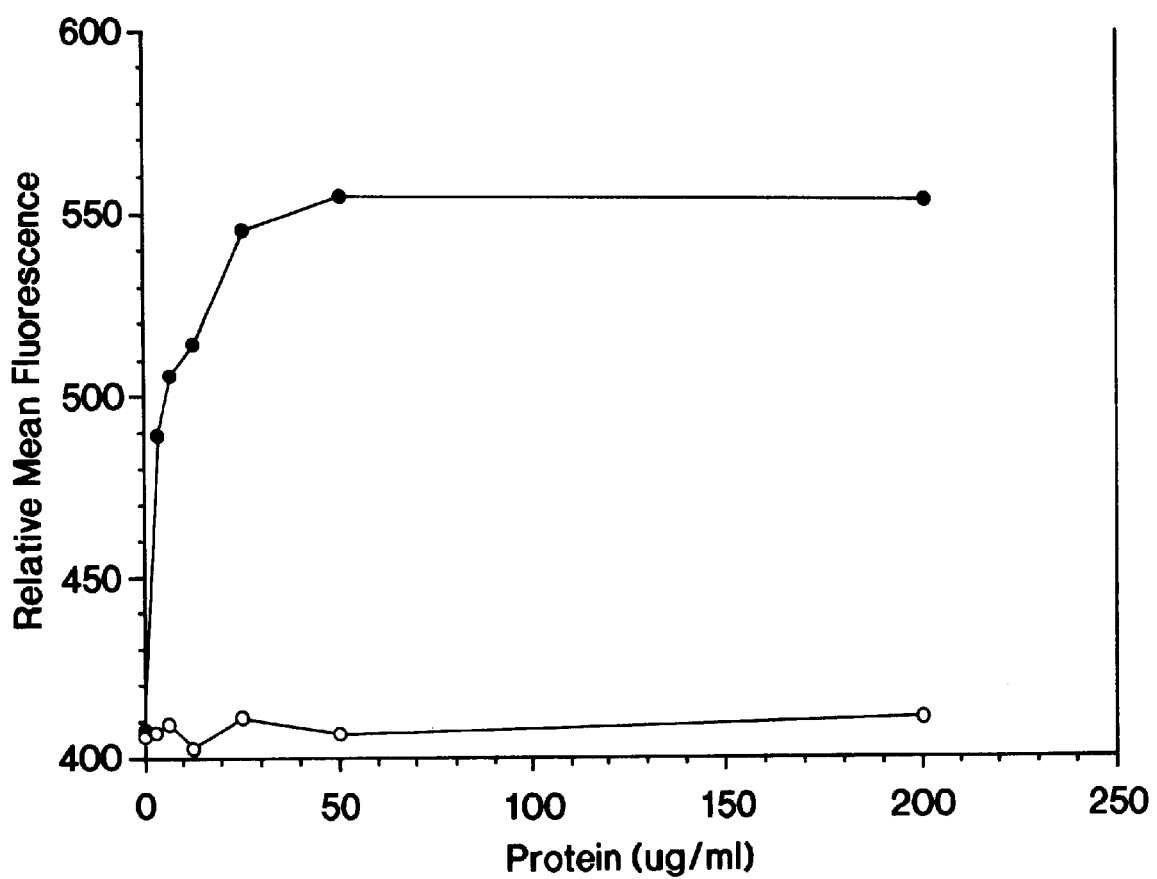
FIG. 5 is a graphical illustration of a comparison of the binding of Spα-mIg (solid circles) and WC1-mIg (open circles) to K-562 cells. Relative mean fluorescence values were obtained from flow cytometric data.

Flow cytometry was used to conduct a systematic examination of the ability of Spα-mIg fusion protein to bind to human cell lines. The myeloid cell line K-562 bound to Spα-mIg but not to a control protein containing the amino terminal three SRCR domains of bovine WC1 fused to the same constant domain of murine IgG2a, WC1-mIg. Binding of Spα to the K-562 cells was concentration dependent and saturable (FIG. 5). Spα-mIg also displayed weaker binding to the myeloid cell line THP1, but not to U-937 cells. Binding of Spα-mIg was also observed on the lymphoma B cell line Raji and also the T cell line Hut78. The Spα-mIg fusion protein, but not WE1-mIg, bound to peripheral blood mononuclear cells (PBMC). Binding of Spα-mIg was not seen on elutriated peripheral blood T cells nor elutriated B cells. The binding of Spα-mIg to elutriated monocytes from different donors could always be detected but showed some degree of variability.

EXAMPLE 4

Preparation of Anti-SpαMonoclonal Antibodies

Immunizations: A 6–8 week old female BALB/c mouse (Taconic, Germantown, N.Y.) was immunized with purified Spα-mIg fusion protein consisting of full-length Spα fused to the hinge, CH2 and CH3 domains of a murine IgG2a antibody. Primary and secondary immunizations were administered intraperitoneally with protein emulsified in Ribi adjuvant (R-730; Ribi ImmunoChem Research, Inc., Hamilton, Mont.). Three days prior to cell fusion, the mouse was immunized intravascularly with fusion protein in PBS.

For hybridoma generation, cells harvested from the spleen and all indentifiable lymph nodes were fused with X63-Af8.65 myeloma cells at a 3:1 ratio of leukocytes:myeloma cells according to the method of Lane (1985) *J. Immunol. Methods* 81:223–228. The resulting post-fusion cell suspension was seeded into 96-well culture plates (Costar) in culture medium consisting of Iscove's modified Dulbecco's medium supplemented with 2 mM L-glutamine, 100 U/mol penicillin, 100 μg/ml streptomycin (all from GIBCO), 10% fetal calf serum, 10% hybridoma cloning factor (BM-Condimed H1; Boehringer-Mannheim, Indianapolis, Ind.) and HAT (GIBCO) as a selective agent for hybridomas.

Master Well Screen: Master wells positive for antibody against SPα were screened using an ELISA assay. The recombinant Spα protein constructs used in the assay are shown below, in which D1, D2 and D3 represent the SRCR domains as shown in FIG. 1. The flag tail is an 8 amino acid long peptide (Kodak) located at the C-terminal end of the Spα protein. Recombinant proteins were produced by transient expression in COS cells (see, e.g., Aruffo et al. (1990) *Cell* 61:1303–1313) and purified using Protein-A column chromatography. A bacterial alkaline phosphatase (BAP) control protein (Kodak No. IB13201) was used as a negative control. Master wells were screened using only the full-length Spα construct. Anti-Spα-positive master wells were then rescreened for domain specificity using the domain-specific Spα constructs depicted below.

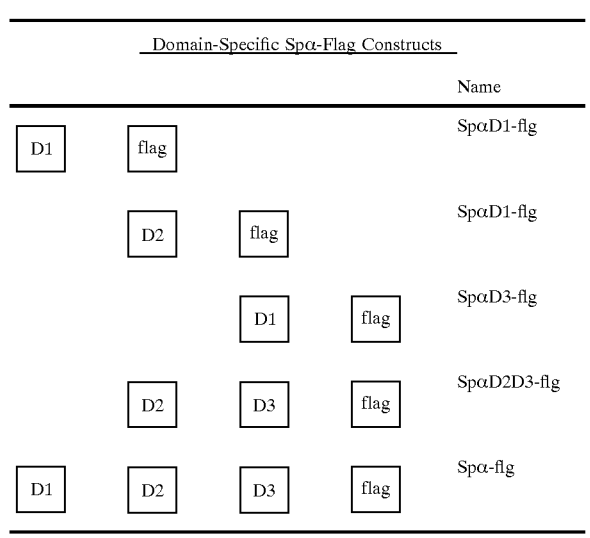

ELISA Assay: 100 μl/well of 300 ng/ml Spα-flg (diluted in PBS) was added to a microtiter plate and incubated overnight at 4° C. The plate was then washed twice with wash buffer (PBS containing 0.05% Tween). Specimen diluent (Genetic Systems Incorporated) was added to each well and the plate was incubated for 1 hr at room temperature, then washed twice with wash buffer. 100 μl/well of master well supernatant was added to each well, and the plate was incubated for 1 hour at room temperature. After washing twice as described above, 100 μl of 1/5000 diluted goat anti-mouse IgG-horse radish peroxidase (Biosource 4404) was added to each well and incubated for 1 hour at room temperature. The plate was again washed twice with wash buffer. To each well, 100 μl 1/100 diluted Chromogen reagent (Genetics Systems Incorporated) was added. After the color had developed, 50 μl 1.0 N $H_2SO_4$ was added and the plate was scanned at 450 nm and 630 nm using an ELISA reader.

The ELISA screen yielded 173 master wells positive for anti-Spα antibody. All 173 positive wells were screened by ELISA for Spα domain specificity.

Monoclonal mouse antibodies were cloned from master wells by limited dilution. Cloned antibodies against Spα are listed in Table 1.

TABLE 1

| Ab designation | Domain Specificity | Isotype |
|---|---|---|
| 1.84C | 3 | IgG2a |
| 1.56B | 3 | IgG1 |
| 1.130B | 2 | IgG1 |
| 1.135F | 2 | IgG1 |
| 1.30B | 1 | IgG1 |
| 1.39C | 1 | IgG1 |
| 1.70D | 1 | IgG2a |

Deposits of Strains Useful in Practicing the Invention

A deposit of biologically pure cultures of the following strains was made with the American Type Culture Collection, 12301 Parklawn Drive, Rockville, Md., under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become nonviable or be inadvertently destroyed, or, in the case of plasmid-containing strains, lose its plasmid, it will be replaced with a viable culture(s) of the same taxonomic description. All restrictions on the availability to the public of the deposited hybridoma cell lines will be irrevocably removed upon the granting of a patent hereon.

Should there be a discrepancy between the sequence presented in the present application and the sequence of the gene of interest in the deposited plasmid due to routine sequencing errors, the sequence in the deposited plasmid controls.

| Strain | Deposit Date | ATCC No. |
|---|---|---|
| Murine hybridoma cell line 1.84C | 2/28/97 | HB-12306 |
| Murine hybridoma cell line 1.130B | 2/28/97 | HB-12307 |
| Murine hybridoma cell line 1.39C | 2/28/97 | HB-12305 |

Thus, a novel SRCR domain-containing polypeptide has been disclosed. Although preferred embodiments of the subject invention have been described in some detail, it is understood that obvious variations can be made without departing from the spirit and the scope of the invention as defined by the appended claims.

We claim:

1. An isolated cDNA molecule that encodes an Spα polypeptide having the amino acid sequence depicted in SEQ ID NO:2.

2. The isolated cDNA molecule of claim 1, wherein the molecule has a nucleic acid sequence as depicted in.

3. An expression vector comprising the cDNA molecule of claim 1 operably linked to control sequences that direct the transcription of the molecule whereby said molecule is expressed in a host cell.

4. A host cell comprising the expression vector of claim 3.

5. A method for producing an Spα polypeptide comprising:

culturing the host cell of claim 4 under conditions that allow the production of the Spα polypeptide; and recovering the Spα polypeptide.

* * * * *

UNITED STATES PATENT AND TRADEMARK OFFICE
CERTIFICATE OF CORRECTION

PATENT NO.    : 6,046,314
DATED         : April 4, 2000
INVENTOR(S)   : Gebe et al.

It is certified that error appears in the above-identified patent and that said Letters Patent is hereby corrected as shown below:

Column 35,
Line 17, after "as depicted in" please insert -- SEQ ID NO:1 --.

Signed and Sealed this

Seventh Day of January, 2003

JAMES E. ROGAN
*Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 2178 base pairs
      (B) TYPE: nucleic acid
      (C) STRANDEDNESS: single
      (D) TOPOLOGY: linear -continued (ii) MOLECULE TYPE: DNA (genomic)

(ix) FEATURE:
    (A) NAME/KEY: CDS
    (B) LOCATION: 64..1101

(xi) SEQUENCE DESCRIPTION: SEQ ID NO:1:

```
CTGCTTGGGG ACCTCCTTCT AGCCTTAAAT TTCAGCTCAT CACCTTCACC TGCCTTGGTC          60

ATG GCT CTG CTA TTC TCC TTG ATC CTT GCC ATT TGC ACC AGA CCT GGA          108
Met Ala Leu Leu Phe Ser Leu Ile Leu Ala Ile Cys Thr Arg Pro Gly
    1               5                  10                  15

TTC CTA GCG TCT CCA TCT GGA GTG CGG CTG GTG GGG GGC CTC CAC CGC          156
Phe Leu Ala Ser Pro Ser Gly Val Arg Leu Val Gly Gly Leu His Arg
                20                  25                  30

TGT GAA GGG CGG GTG GAG GTG GAA CAG AAA GGC CAG TGG GGC ACC GTG          204
Cys Glu Gly Arg Val Glu Val Glu Gln Lys Gly Gln Trp Gly Thr Val
                    35                  40                  45

TGT GAT GAC GGC TGG GAC ATT AAG GAC GTG GCT GTG TTG TGC CGG GAG          252
Cys Asp Asp Gly Trp Asp Ile Lys Asp Val Ala Val Leu Cys Arg Glu
                50                  55                  60

CTG GGC TGT GGA GCT GCC AGC GGA ACC CCT AGT GGT ATT TTG TAT GAG          300
Leu Gly Cys Gly Ala Ala Ser Gly Thr Pro Ser Gly Ile Leu Tyr Glu
65                  70                  75

CCA CCA GCA GAA AAA GAG CAA AAG GTC CTC ATC CAA TCA GTC AGT TGC          348
Pro Pro Ala Glu Lys Glu Gln Lys Val Leu Ile Gln Ser Val Ser Cys
80                  85                  90                  95

ACA GGA ACA GAA GAT ACA TTG GCT CAG TGT GAG CAA GAA GAA GTT TAT          396
Thr Gly Thr Glu Asp Thr Leu Ala Gln Cys Glu Gln Glu Glu Val Tyr
                    100                 105                 110

GAT TGT TCA CAT GAT GAA GAT GCT GGG GCA TCG TGT GAG AAC CCA GAG          444
Asp Cys Ser His Asp Glu Asp Ala Gly Ala Ser Cys Glu Asn Pro Glu
                115                 120                 125

AGC TCT TTC TCC CCA GTC CCA GAG GGT GTC AGG CTG GCT GAC GGC CCT          492
Ser Ser Phe Ser Pro Val Pro Glu Gly Val Arg Leu Ala Asp Gly Pro
            130                 135                 140

GGG CAT TGC AAG GGA CGC GTG GAA GTG AAG CAC CAG AAC CAG TGG TAT          540
Gly His Cys Lys Gly Arg Val Glu Val Lys His Gln Asn Gln Trp Tyr
        145                 150                 155

ACC GTG TGC CAG ACA GGC TGG AGC CTC CGG GCC GCA AAG GTG GTG TGC          588
Thr Val Cys Gln Thr Gly Trp Ser Leu Arg Ala Ala Lys Val Val Cys
160                 165                 170                 175

CGG CAG CTG GGA TGT GGG AGG GCT GTA CTG ACT CAA AAA CGC TGC AAC          636
Arg Gln Leu Gly Cys Gly Arg Ala Val Leu Thr Gln Lys Arg Cys Asn
                180                 185                 190

AAG CAT GCC TAT GGC CGA AAA CCC ATC TGG CTG AGC CAG ATG TCA TGC          684
Lys His Ala Tyr Gly Arg Lys Pro Ile Trp Leu Ser Gln Met Ser Cys
                195                 200                 205

TCA GGA CGA GAA GCA ACC CTT CAG GAT TGC CCT TCT GGG CCT TGG GGG          732
Ser Gly Arg Glu Ala Thr Leu Gln Asp Cys Pro Ser Gly Pro Trp Gly
            210                 215                 220

AAG AAC ACC TGC AAC CAT GAT GAA GAC ACG TGG GTC GAA TGT GAA GAT          780
Lys Asn Thr Cys Asn His Asp Glu Asp Thr Trp Val Glu Cys Glu Asp
        225                 230                 235

CCC TTT GAC TTG AGA CTA GTA GGA GGA GAC AAC CTC TGC TCT GGG CGA          828
Pro Phe Asp Leu Arg Leu Val Gly Gly Asp Asn Leu Cys Ser Gly Arg
240                 245                 250                 255

CTG GAG GTG CTG CAC AAG GGC GTA TGG GGC TCT GTC TGT GAT GAC AAC          876
Leu Glu Val Leu His Lys Gly Val Trp Gly Ser Val Cys Asp Asp Asn
                260                 265                 270
```

-continued

```
TGG GGA GAA AAG GAG GAC CAG GTG GTA TGC AAG CAA CTG GGC TGT GGG    924
Trp Gly Glu Lys Glu Asp Gln Val Val Cys Lys Gln Leu Gly Cys Gly
            275                 280                 285

AAG TCC CTC TCT CCC TCC TTC AGA GAC CGG AAA TGC TAT GGC CCT GGG    972
Lys Ser Leu Ser Pro Ser Phe Arg Asp Arg Lys Cys Tyr Gly Pro Gly
            290                 295                 300

GTT GGC CGC ATC TGG CTG GAT AAT GTT CGT TGC TCA GGG GAG GAG CAG   1020
Val Gly Arg Ile Trp Leu Asp Asn Val Arg Cys Ser Gly Glu Glu Gln
        305                 310                 315

TCC CTG GAG CAG TGC CAG CAC AGA TTT TGG GGG TTT CAC GAC TGC ACC   1068
Ser Leu Glu Gln Cys Gln His Arg Phe Trp Gly Phe His Asp Cys Thr
320                 325                 330                 335

CAC CAG GAA GAT GTG GCT GTC ATC TGC TCA GGA TAGTATCCTG GTGTTGCTTG 1121
His Gln Glu Asp Val Ala Val Ile Cys Ser Gly
                340                 345

ACCTGGCCCC CCTGGCCCCG CCTGCCCTCT GCTTGTTCTC CTGAGCCCTG ATTATCCTCA 1181

TACTCATTCT GGGGCTCAGG CTTGAGCCAC TACTCCCTCA TCCCCTCAGG AGTCTGAACA 1241

CTGGGCTTAT GCCTTACTCT CAGGGACAAG CAGCCCCCTT TGCTGCCTGT AGATGTGAGC 1301

TGTTGAGTTC CCTCTTGCTG GGAAGATGA GCTTCCATGT ATCCTGTGCT CAACCCTGAC  1361

CCTTTGACAC TGGTTCTGGC CTTTCCTGCC TTTTCTCAAG CTGCCTGGAA TCCTCAAACC 1421

TGTCACTTTG GTCAGATGTG CAGACCATTA CTAAGGTCTA TGTCTGCAAA CATTACTAAT 1481

CTAGGTCCTA TTACTAATCT ATGTCTGCAA ACATTAAAGG AATGAAACAA TGAAAGGAAC 1541

ATTTGAAAGA AAATGTGGGT AGACAATTTC TTGCAACTTG GGGGAAAGTT TAGAATTCTT 1601

TTGATTGGAC TACTTTTTTT TTTTTCCTCA AGCTTCAGGT GACCACAATA GCAACACCTC 1661

CCTATTCTGT TATTTCTTAG TGTAGGTAGA CAATTCTTTC AGGAGCAGAG CAGCGTCCTA 1721

TAATCCTAGA CCTTTTCATG ACGTGTAAAA AATGATGTTT CATCCTCTGA TTGCCCCAAT 1781

AAAAATCTTT GTTGTCCATC CCTATACAAC CTGCCAACAT GGTTGACATT AATGAGAGGA 1841

ATGTCAAAAA TACATTTTAC TTTATTCAAA GAAAATATA TTGGTTACTG GAAAAGGTC   1901

AAGAAAGAGG CAGAAAGAGA TCAGGGAGGG CTAAAGTTGT GTCTTATGCC AAGCGGAAGT 1961

GGAAAATATC ACTTTTCACT TTATCAACTG AGACTTTGGG GCCTGTAAGC TTGAGGCAAG 2021

ACAGAAATAA GAGAATCAAG ACTTGATTGT AAAAATTGAC AACTTTAGAT TCTGAGGCTA 2081

GGCTGAGTAC TTATTATACG GCTACATTAC ACATTTAACT TATCTAATAA ATCAGATTTC 2141

ACAGTCTCAA AAAAAAAAAA AGAAAAAAAA AAAAAAA                           2178

(2) INFORMATION FOR SEQ ID NO:2:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:2:

Ala Leu Leu Phe Ser Leu Ile Leu Ala Ile Cys Thr Arg Pro Gly Phe
 1               5                  10                  15

Leu Ala Ser Pro Ser Gly Val Arg Leu Val Gly Leu His Arg Cys
            20                  25                  30

Glu Gly Arg Val Glu Val Glu Gln Lys Gly Gln Trp Gly Thr Val Cys
        35                  40                  45

Asp Asp Gly Trp Asp Ile Lys Asp Val Ala Val Leu Cys Arg Glu Leu
    50                  55                  60
```

```
Gly Cys Gly Ala Ala Ser Gly Thr Pro Ser Gly Ile Leu Tyr Glu Pro
 65                  70                  75                  80

Pro Ala Glu Lys Glu Gln Lys Val Leu Ile Gln Ser Val Ser Cys Thr
                 85                  90                  95

Gly Thr Glu Asp Thr Leu Ala Gln Cys Glu Gln Glu Val Tyr Asp
             100                 105                 110

Cys Ser His Asp Glu Asp Ala Gly Ser Cys Glu Asn Pro Glu Ser
         115                 120                 125

Ser Phe Ser Pro Val Pro Glu Gly Val Arg Leu Ala Asp Gly Pro Gly
    130                 135                 140

His Cys Lys Gly Arg Val Glu Val Lys His Gln Asn Gln Trp Tyr Thr
145                 150                 155                 160

Val Cys Gln Thr Gly Trp Ser Leu Arg Ala Ala Lys Val Val Cys Arg
                165                 170                 175

Gln Leu Gly Cys Gly Arg Ala Val Leu Thr Gln Lys Arg Cys Asn Lys
                180                 185                 190

His Ala Tyr Gly Arg Lys Pro Ile Trp Leu Ser Gln Met Ser Cys Ser
        195                 200                 205

Gly Arg Glu Ala Thr Leu Gln Asp Cys Pro Ser Gly Pro Trp Gly Lys
210                 215                 220

Asn Thr Cys Asn His Asp Glu Asp Thr Trp Val Glu Cys Glu Asp Pro
225                 230                 235                 240

Phe Asp Leu Arg Leu Val Gly Gly Asp Asn Leu Cys Ser Gly Arg Leu
                245                 250                 255

Glu Val Leu His Lys Gly Val Trp Gly Ser Val Cys Asp Asp Asn Trp
            260                 265                 270

Gly Glu Lys Glu Asp Gln Val Val Cys Lys Gln Leu Gly Cys Gly Lys
            275                 280                 285

Ser Leu Ser Pro Ser Phe Arg Asp Arg Lys Cys Tyr Gly Pro Gly Val
    290                 295                 300

Gly Arg Ile Trp Leu Asp Asn Val Arg Cys Ser Gly Glu Glu Gln Ser
305                 310                 315                 320

Leu Glu Gln Cys Gln His Arg Phe Trp Gly Phe His Asp Cys Thr His
                325                 330                 335

Gln Glu Asp Val Ala Val Ile Cys Ser Gly
            340                 345

(2) INFORMATION FOR SEQ ID NO:3:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

Arg Leu Val Gly Gly Leu His Arg Cys Glu Gly Arg Val Glu Val Glu
 1               5                  10                  15

Gln Lys Gly Gln Trp Gly Thr Val Cys Asp Asp Gly Trp Asp Ile Lys
                20                  25                  30

Asp Val Ala Val Leu Cys Arg Glu Leu Gly Cys Gly Ala Ala Ser Gly
            35                  40                  45

Thr Pro Ser Gly Ile Leu Tyr Glu Pro Pro Ala Glu Lys Glu Gln Lys
    50                  55                  60
```

```
Val Leu Ile Gln Ser Val Ser Cys Thr Gly Thr Glu Asp Thr Leu Ala
65                  70                  75                  80

Gln Cys Glu Gln Glu Glu Val Tyr Asp Cys Ser His Asp Glu Asp Ala
                85                  90                  95

Gly Ala Ser Cys Glu
            100
```

(2) INFORMATION FOR SEQ ID NO:4:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
Arg Leu Ala Asp Gly Pro Gly His Cys Lys Gly Arg Val Glu Val Lys
1               5                   10                  15

His Gln Asn Gln Trp Tyr Thr Val Cys Gln Thr Gly Trp Ser Leu Arg
                20                  25                  30

Ala Ala Lys Val Val Cys Arg Gln Leu Gly Cys Gly Arg Ala Val Leu
            35                  40                  45

Thr Gln Lys Arg Cys Asn Lys His Ala Tyr Gly Arg Lys Pro Ile Trp
50                  55                  60

Leu Ser Gln Met Ser Cys Ser Gly Arg Glu Ala Thr Leu Gln Asp Cys
65                  70                  75                  80

Pro Ser Gly Pro Trp Gly Lys Asn Thr Cys Asn His Asp Glu Asp Thr
                85                  90                  95

Trp Val Glu Cys Glu
            100
```

(2) INFORMATION FOR SEQ ID NO:5:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
Arg Leu Val Gly Gly Asp Asn Leu Cys Ser Gly Arg Leu Glu Val Leu
1               5                   10                  15

His Lys Gly Val Trp Gly Ser Val Cys Asp Asp Asn Trp Gly Glu Lys
                20                  25                  30

Glu Asp Gln Val Val Cys Lys Gln Leu Gly Cys Gly Lys Ser Leu Ser
            35                  40                  45

Pro Ser Phe Arg Asp Arg Lys Cys Tyr Gly Pro Gly Val Gly Arg Ile
50                  55                  60

Trp Leu Asp Asn Val Arg Cys Ser Gly Glu Glu Gln Ser Leu Glu Gln
65                  70                  75                  80

Cys Gln His Arg Phe Trp Gly Phe His Asp Cys Thr His Gln Glu Asp
                85                  90                  95

Val Ala Val Ile Cys Ser
            100
```

(2) INFORMATION FOR SEQ ID NO:6:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
Arg Leu Thr Asn Gly Ser Ser Cys Ser Gly Thr Val Glu Val Arg
1               5                  10                  15

Leu Glu Ala Ser Trp Glu Pro Ala Cys Gly Ala Leu Trp Asp Ser Arg
            20                  25                  30

Ala Ala Glu Ala Val Cys Arg Ala Leu Gly Cys Gly Ala Glu Ala
        35                  40                  45

Ala Ser Gln Leu Ala Pro Pro Thr Pro Glu Leu Pro Pro Pro Ala
50                  55                  60

Ala Gly Asn Thr Ser Val Ala Ala Asn Ala Thr Leu Ala Gly Ala Pro
65                  70                  75                  80

Ala Leu Leu Cys Ser Gly Ala Glu Trp Arg Leu Cys Glu Val Val Glu
                85                  90                  95

His Ala Cys Arg Ser Asp Gly Arg Ala Arg Val Thr Cys Ala
            100                 105                 110
```

(2) INFORMATION FOR SEQ ID NO:7:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
Arg Leu Val Asp Gly Gly Gly Ala Cys Ala Gly Arg Val Glu Met Leu
1               5                  10                  15

Glu His Gly Glu Trp Gly Ser Val Cys Asp Asp Thr Trp Asp Leu Glu
            20                  25                  30

Asp Ala His Val Val Cys Arg Gln Leu Gly Cys Gly Trp Ala Pro Gly
        35                  40                  45

Leu His Phe Thr Pro Gly Arg Gly Pro Ile His Arg Asp Gln Val Asn
50                  55                  60

Cys Ser Gly Ala Glu Ala Tyr Leu Trp Asp Cys Pro Gly Leu Pro Gly
65                  70                  75                  80

Gln His Tyr Cys Gly His Lys Glu Asp Ala Gly Val Val Cys Ser
                85                  90                  95
```

(2) INFORMATION FOR SEQ ID NO:8:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
Arg Leu Thr Gly Gly Ala Asp Arg Cys Glu Gly Gln Val Glu Val His
1               5                  10                  15
```

```
Phe Arg Gly Val Trp Asn Thr Val Cys Asp Ser Glu Trp Tyr Pro Ser
            20                  25                  30

Glu Ala Lys Val Leu Cys Gln Ser Leu Gly Cys Gly Thr Ala Val Glu
            35                  40                  45

Arg Pro Lys Gly Leu Pro His Ser Leu Ser Gly Arg Met Tyr Tyr Ser
            50                  55                  60

Cys Asn Gly Glu Glu Leu Thr Leu Ser Asn Cys Ser Trp Arg Phe Asn
 65                  70                  75                  80

Asn Ser Asn Leu Cys Ser Gln Ser Leu Ala Ala Arg Val Leu Cys Ser
                85                  90                  95
```

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
Arg Leu Val Asp Gly Glu Asn Lys Cys Ser Gly Arg Val Glu Val Lys
 1               5                  10                  15

Val Gln Glu Glu Trp Gly Thr Val Cys Asn Asn Gly Trp Ser Met Glu
            20                  25                  30

Ala Val Ser Val Ile Cys Asn Gln Leu Gly Cys Pro Thr Ala Ile Lys
            35                  40                  45

Ala Pro Gly Trp Ala Asn Ser Ser Ala Gly Ser Gly Arg Ile Trp Met
            50                  55                  60

Asp His Val Ser Cys Arg Gly Asn Glu Ser Ala Leu Trp Asp Cys Lys
 65                  70                  75                  80

His Asp Gly Trp Gly Lys His Ser Asn Cys Thr His Gln Gln Asp Ala
                85                  90                  95

Gly Val Thr Cys Ser
            100
```

(2) INFORMATION FOR SEQ ID NO:10:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
Arg Leu Thr Arg Gly Gly Asn Met Cys Ser Gly Arg Ile Glu Ile Lys
 1               5                  10                  15

Phe Gln Gly Arg Trp Gly Thr Val Cys Asp Asp Asn Phe Asn Ile Asp
            20                  25                  30

His Ala Ser Val Ile Cys Arg Gln Leu Glu Cys Gly Ser Ala Val Ser
            35                  40                  45

Phe Ser Gly Ser Ser Asn Phe Gly Glu Gly Ser Gly Pro Ile Trp Phe
            50                  55                  60

Asp Asp Leu Ile Cys Asn Gly Asn Glu Ser Ala Leu Trp Asn Cys Lys
 65                  70                  75                  80
```

His Gln Gly Trp Gly Lys His Asn Cys Asp His Ala Glu Asp Ala Gly
                85                  90                  95

Val Ile Cys Ser
            100

(2) INFORMATION FOR SEQ ID NO:11:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

Arg Leu Val Asp Gly Val Thr Glu Cys Ser Gly Arg Leu Glu Val Arg
1               5                   10                  15

Phe Gln Gly Glu Trp Gly Thr Ile Cys Asp Asp Gly Trp Asp Ser Tyr
                20                  25                  30

Asp Ala Ala Val Ala Cys Lys Gln Leu Gly Cys Pro Thr Ala Val Thr
            35                  40                  45

Ala Ile Gly Arg Val Asn Ala Ser Lys Gly Phe Gly His Ile Trp Leu
        50                  55                  60

Asp Ser Val Ser Cys Gln Gly His Glu Pro Ala Val Trp Gln Cys Lys
65                  70                  75                  80

His His Glu Trp Gly Lys His Tyr Cys Asn His Asn Glu Asp Ala Gly
                85                  90                  95

Val Thr Cys Ser
            100

(2) INFORMATION FOR SEQ ID NO:12:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

Arg Leu Arg Gly Gly Gly Ser Arg Cys Ala Gly Thr Val Glu Val Glu
1               5                   10                  15

Ile Gln Arg Leu Leu Gly Lys Val Cys Asp Arg Gly Trp Gly Leu Lys
                20                  25                  30

Glu Ala Asp Val Val Cys Arg Gln Leu Gly Cys Gly Ser Ala Leu Lys
            35                  40                  45

Thr Ser Tyr Gln Val Tyr Ser Lys Ile Gln Ala Thr Asn Thr Trp Leu
        50                  55                  60

Phe Leu Ser Ser Cys Asn Gly Asn Glu Thr Ser Leu Trp Asp Cys Lys
65                  70                  75                  80

Asn Trp Gln Trp Gly Gly Leu Thr Cys Asp His Tyr Glu Glu Ala Lys
                85                  90                  95

Ile Thr Cys Ser
            100

(2) INFORMATION FOR SEQ ID NO:13:

(i) SEQUENCE CHARACTERISTICS:
        (A) LENGTH: 100 amino acids (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

Arg Leu Val Gly Gly Asp Ile Pro Cys Ser Gly Arg Val Glu Val Lys
1               5                   10                  15

His Gly Asp Thr Trp Gly Ser Ile Cys Asp Ser Asp Phe Ser Leu Glu
            20                  25                  30

Ala Ala Ser Val Leu Cys Arg Glu Leu Gln Cys Gly Thr Val Val Ser
        35                  40                  45

Ile Leu Gly Gly Ala His Phe Gly Glu Gly Asn Gly Gln Ile Trp Ala
    50                  55                  60

Glu Glu Phe Gln Cys Glu Gly His Glu Ser His Leu Ser Leu Cys Pro
65                  70                  75                  80

Val Ala Pro Arg Pro Glu Gly Thr Cys Ser His Ser Arg Asp Val Gly
                85                  90                  95

Val Val Cys Ser
            100

(2) INFORMATION FOR SEQ ID NO:14:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

Arg Leu Val Asn Gly Lys Thr Pro Cys Glu Gly Arg Val Glu Leu Lys
1               5                   10                  15

Thr Leu Gly Ala Trp Gly Ser Leu Cys Asn Ser His Trp Asp Ile Glu
            20                  25                  30

Asp Ala His Val Leu Cys Gln Gln Leu Lys Cys Gly Val Ala Leu Ser
        35                  40                  45

Thr Pro Gly Gly Ala Arg Phe Gly Lys Gly Asn Gly Gln Ile Trp Arg
    50                  55                  60

His Met Phe His Cys Thr Gly Thr Glu Gln His Met Gly Asp Cys Pro
65                  70                  75                  80

Val Thr Ala Leu Gly Ala Ser Leu Cys Pro Ser Glu Gln Val Ala Ser
                85                  90                  95

Val Ile Cys Ser
            100

(2) INFORMATION FOR SEQ ID NO:15:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

Arg Leu Val Asn Gly Gly Gly Arg Cys Ala Gly Arg Val Glu Ile Tyr
1               5                   10                  15

```
His Glu Gly Ser Trp Gly Thr Ile Cys Asp Asp Ser Trp Asp Leu Ser
            20                  25                  30

Asp Ala His Val Val Cys Arg Gln Leu Gly Cys Gly Glu Ala Ile Asn
            35                  40                  45

Ala Thr Gly Ser Ala His Phe Gly Glu Gly Thr Gly Pro Ile Trp Leu
 50                      55                  60

Asp Glu Met Lys Cys Asn Gly Lys Glu Ser Arg Ile Trp Gln Cys His
 65                  70                  75                  80

Ser His Gly Trp Gly Gln Gln Asn Cys Arg His Lys Glu Asp Ala Gly
                85                  90                  95

Val Ile Cys Ser
            100

(2) INFORMATION FOR SEQ ID NO:16:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

Arg Leu Thr Ser Glu Ala Ser Arg Glu Ala Cys Ala Gly Arg Leu Glu
 1               5                  10                  15

Val Phe Tyr Asn Gly Ala Trp Gly Thr Val Gly Lys Ser Ser Met Ser
            20                  25                  30

Glu Thr Thr Val Gly Val Val Cys Arg Gln Leu Gly Cys Ala Asp Lys
            35                  40                  45

Gly Lys Ile Asn Pro Ala Ser Leu Asp Lys Ala Met Ser Ile Pro Met
 50                  55                  60

Trp Val Asp Asn Val Gln Cys Pro Lys Gly Pro Asp Thr Leu Trp Gln
 65                  70                  75                  80

Cys Pro Ser Ser Pro Trp Glu Lys Arg Leu Ala Ser Pro Ser Glu Glu
                85                  90                  95

Thr Trp Ile Thr Cys Asp
            100

(2) INFORMATION FOR SEQ ID NO:17:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

Arg Leu Gln Glu Gly Pro Thr Ser Cys Ser Gly Arg Val Glu Ile Trp
 1               5                  10                  15

His Gly Gly Ser Trp Gly Thr Val Cys Asp Asp Ser Trp Asp Leu Asp
            20                  25                  30

Asp Ala Gln Val Val Cys Gln Gln Leu Gly Cys Gly Pro Ala Leu Lys
            35                  40                  45

Ala Phe Lys Glu Ala Glu Phe Gly Gln Gly Thr Gly Pro Ile Trp Leu
 50                      55                  60
```

-continued

```
Asn Glu Val Lys Cys Lys Gly Asn Glu Ser Ser Leu Trp Asp Cys Pro
 65              70                  75                  80

Ala Arg Arg Trp Gly His Ser Glu Cys Gly His Lys Glu Asp Ala Ala
                 85                  90                  95

Val Asn Cys Thr
            100
```